(12) United States Patent
Harn et al.

(10) Patent No.: US 9,044,444 B2
(45) Date of Patent: Jun. 2, 2015

(54) METHOD FOR IMPROVING SKIN APPEARANCE AND REDUCING HAIR LOSS

(75) Inventors: Horng-Jyh Harn, Taichung (TW); Shinn-Zong Lin, Taichung (TW); Tzyy-Wen Chiou, Taichung (TW); Po-Cheng Lin, Taichung (TW); Hen-Yi Chu, Taichung (TW)

(73) Assignee: CHINA MEDICAL UNIVERSITY, Taichung (TW)

( * ) Notice: Subject to any disclaimer, the term of this patent is extended or adjusted under 35 U.S.C. 154(b) by 38 days.

(21) Appl. No.: 13/527,984

(22) Filed: Jun. 20, 2012

(65) Prior Publication Data

US 2013/0287717 A1    Oct. 31, 2013

(30) Foreign Application Priority Data

Apr. 26, 2012   (TW) .............................. 101114923 A

(51) Int. Cl.
*A01N 63/00*   (2006.01)
*A61K 38/20*   (2006.01)
*A61K 38/19*   (2006.01)

(52) U.S. Cl.
CPC ............. *A61K 38/202* (2013.01); *A61K 38/193* (2013.01)

(58) Field of Classification Search
CPC ................................ C07K 14/56; C07K 16/24
USPC ................................................. 424/93.7, 534
See application file for complete search history.

(56) References Cited

U.S. PATENT DOCUMENTS

| 5,135,913 A * | 8/1992 | Pickart .......................... 514/18.8 |
| 6,790,440 B2 * | 9/2004 | Hellstrand et al. ........... 424/85.1 |
| 2012/0039856 A1 * | 2/2012 | Han .............................. 424/93.7 |

FOREIGN PATENT DOCUMENTS

WO   WO 2005065269 A2 *   7/2005
WO   WO 2006071011 A1 *   7/2006

OTHER PUBLICATIONS

Skoutelis, Alexandra et al. Angiogenic Activity is Defective in Monocytes from Patients with Alopecia Universalis. The Journal of Investigative Dermatology (95). pp. 139-143. 1990.*
Bernhard, Helga et al. Generation of Immunostimulatory Dendritic Cells from Human CD34+ Hematopoietic Progenitor Cells of the Bone Marrow and Peripheral Blood. Cancer Research 55. pp. 1099-1104. 1995.*
Asnis, Lisa et al. Cutaneous Reactions to Recombinant Cytokine Therapy. Journal of the American Academy of Dermatology. vol. 33, No. 3. 1995. pp. 393-410.*
Arpinati, Mario et. al. Granulocyte-Colony Stimulating Factor Mobilizes T-helper 2-inducing Dendritic Cells. Blood: American Society of Hematology. 2000. (95) pp. 2484-2490.*
Chaiworapongsa, Tinnakorn et al. The Role of Granulocyte Colony-Stimulating Factor in the Neutrophilia Observed in the Fetal Inflammatory Response Syndrome. Journal of Perinat Medicine. Nov. 2011. 39(6): pp. 653-666.*
ACS. Stem Cell Transplant (Peripheral Blood, Bone Marrow, and Cord Blood Transplants). 2013 American Cancer Society. pp. 1-35.*
The 8th Asia Pacific Symposium on Neural Regeneration in conjunction with The 5th Pan Pacific Symposium on Stem Cells and Cancer Research in Taipei, Taiwan on Apr. 13, 2012; Conference agenda (see p. 1) and the presentation summary of The 8th Asia Pacific Symposium on Neural Regeneration in conjunction with The 5th Pan Pacific Symposium on Stem Cells and Cancer Research in Taipei, Taiwan on Apr. 13, 2012.
Executed Declaration under 37 C.F.R. 1.321 of Horng-Jyh Harn discussing authorship of the paper entitled The 8th Asia Pacific Symposium on Neural Regeneration in conjunction with The 5th Pan Pacific Symposium on Stem Cells and Cancer Research in Taipei, Taiwan on Apr. 13, 2012.
Mielcarek, M et al., CD14+ cells in granulocyte colony-stimulating factor (G-CSF)-mobilized peripheral blood mononuclear cells induce secretion of interleukin-6 and G-CSF by marrow stroma. 1996; Blood 87: 574-580. American Society of Hematology, Washington, DC.
Hasegawa, M. et al. Enhanced production of interleukin-6 (IL-6), oncostatin M and soluble IL-6 receptor by cultured peripheral blood mononuclear cells from patients with systemic sclerosis. 1999; Rheumatology 38: 612-617. British Society for Rheumatology.

* cited by examiner

*Primary Examiner* — Susan Hanley
*Assistant Examiner* — Nghi Nguyen
(74) *Attorney, Agent, or Firm* — Michael W. Ferrell; Ferrells, PLLC; Anna L. Kinney

(57) ABSTRACT

A method for improving skin appearance and/or reducing hair loss in a subject is provided. The method comprises administrating to the subject an effective amount of peripheral monocytes, wherein the peripheral monocytes are induced by granulocyte colony stimulating factor (GCSF) or a combination of GCSF and an interleukin relative to GCSF.

11 Claims, 8 Drawing Sheets
(8 of 8 Drawing Sheet(s) Filed in Color)

METHOD FOR IMPROVING SKIN APPEARANCE AND REDUCING HAIR LOSS

CLAIM FOR PRIORITY

This application claims the benefit of Taiwan Patent Application No. 101114923, filed on Apr. 26, 2012, in the Taiwan Intellectual Property Office, the disclosure of which is incorporated herein in its entirety by reference.

CROSS-REFERENCES TO RELATED APPLICATIONS

Not applicable.

BACKGROUND OF THE INVENTION

1. Field of the Invention

The present invention relates to a method for improving the appearance of skin and/or reducing hair loss of a subject, especially a method for improving skin aging of a subject, comprising administrating to the subject an effective amount of peripheral monocytes induced by granulocyte colony stimulating factor (GCSF) or a combination of GCSF and an interleukin relative to GCSF.

2. Descriptions of the Related Art

Skin aging can be divided into two categories, intrinsic aging and photo aging, according to the pathway of skin aging. Intrinsic aging of skin is mainly controlled by chromosomes, and the medical technology nowadays still cannot stop the progression of intrinsic aging by modifying the chromosome. Aging can only be stopped by avoiding some known aggravating factors, for example, preventing the exposure of skin to hazardous substances. These two skin aging pathways can also be differentiated by skin area covered by clothes and skin area frequently exposed to the sun, and result in different levels of skin aging. The decrease in the number of keratinocyte stem cells can be observed in intrinsic aging. The microstructure of intrinsic aging shows the loss of natural moisturizing factors in epidermis, the thickening and accumulation of the stratum corneum, disorders of basal cells, occurrence of age spots, pigmented spots and skin darkening due to the increase of melanin, flat papillary layer in the dermis, decrease of hyaluronic acid, denaturation of elastic fibers, derangement of elastic protein, decrease of collagen, etc., gradually causing the unevenness of skin and the loss of tension and elasticity, and eventually results in skin wrinkles or skin flaccidity, thinning of the subcutaneous fat, decreased secretion of sebaceous glands, decreased function of sebum membrane, deterioration of the skin protection ability and skin moisturizing ability, etc.

Over recent years, many developed countries have developed various medical cosmetic approaches to improve skin aging, including medication treatment, cosmetics application, surgical treatment, ablative treatment, injection treatment, non-ablative rejuvenation treatment, etc. However, the molecular structures of some ingredients contained in these medications or cosmetics, such as collagen, elastin, hydrolyzed protein, mucopolysaccharide, hyaluronic acid, and vitamin E, are too large to be absorbed by skin into the dermis, and thus, these ingredients can only stay in the epidermis to retain moisture. Surgical treatment, ablative treatment, and injection treatment, such as chemical peel, microdermabrasion, laser spot removers, laser resurfacing, and wrinkle removing, can renew aging skin and achieve the purpose of regeneration of new skin, but these treatments will cause trauma and slow skin recovery, resulting in various postoperative complications. The injection of collagen can only temporarily fill dermal tissue to eliminate wrinkles and the effect is maintained for no longer than nine months. Laser and radiofrequency for the non-ablative rejuvenation treatment may cause complications such as post-inflammatory hyperpigmentation and scars.

Stem cells are used to treat damaged organs; this method is the latest therapy in the medical field. Hematopoiesis stem cell (HSC) is a pluripotent stem cell in the bone marrow, which can differentiate into monocytes, granules balls, lymphocytes, red blood cells, and platelets. Among the sources of hematopoietic stem cells, peripheral blood stem cells (PBSC) are relatively easy to be obtained, and the collection of peripheral blood stem cells causes less physical injury to the donor. Peripheral blood stem cells have not been applied to improve skin aging to date.

The inventors of the present application found that the peripheral monocytes from peripheral blood stem cells have the effects of improving skin appearance (e.g., improving skin aging) and reducing hair loss, and thus, can be used to reduce the striae (such as forehead wrinkles and nasolabial folds) on the skin, reduce wrinkles, prevent wrinkles, reduce discoloration of skin, improve the color of skin, whiten skin, reduce skin pigmentation, promote the activation of hair follicle cells, promote hair growth, etc.

SUMMARY OF THE INVENTION

The primary objective of this invention is to provide a method for at least one of improving skin appearance and reducing hair loss of a subject, comprising administrating to the subject an effective amount of peripheral monocytes, wherein the peripheral monocytes are induced by granulocyte colony stimulating factor (GCSF) or a combination of GCSF and an interleukin relative to GCSF.

Another objective of this invention is to provide use of peripheral monocytes induced by granulocyte colony stimulating factor or a combination of GCSF and an interleukin relative to GCSF in improving skin appearance and reducing hair loss.

Still another objective of this invention is to provide a composition comprising the peripheral monocytes induced by granulocyte colony stimulating factor (GCSF) or a combination of GCSF and an interleukin relative to GCSF.

The detailed technology and preferred embodiments implemented for the subject invention are described in the following paragraphs accompanying the appended drawings for people skilled in this field to well appreciate the features of the claimed invention.

BRIEF DESCRIPTION OF THE DRAWINGS

The file of this patent contains at least one drawing executed in color. Copies of this patent with color drawings will be provided by the Patent and Trademark Office upon request and payment of the necessary fee.

DETAILED DESCRIPTION OF THE INVENTION

Figure 1:
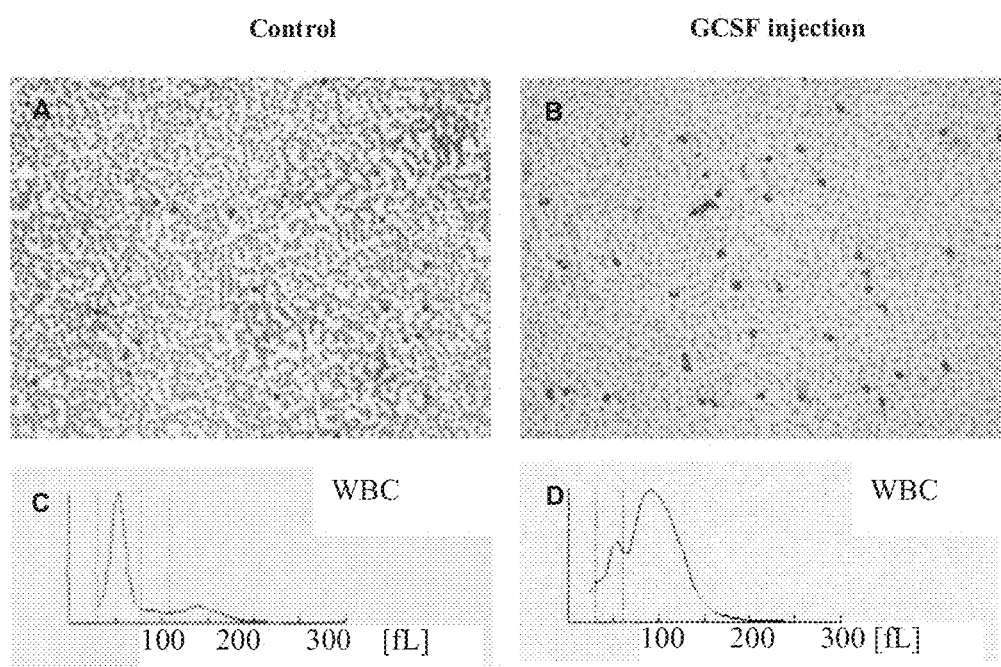
FIG. 1A is a slide picture showing whole blood cells of a male Lanyu pig.
FIG. 1B is a slide picture showing whole blood cells of a male Lanyu pig injected with GCSF.
FIG. 1C is an analytical diagram showing the content of the white blood cells in the entire blood of a male Lanyu pig.
FIG. 1D is an analytical diagram showing the content of the white blood cells in the entire blood of a male Lanyu pig injected with GCSF.

Unless otherwise stated herein, the terms "a (an)", "the" or the like used in this specification (especially in the Claims hereinafter) shall be understood to encompass both the singular form and the plural form.

The inventors of the present application found that peripheral monocytes have the effects of improving skin appearance and reducing hair loss, especially improving skin aging. Hence, the present invention provides a method for improving the skin appearance and reducing hair loss of a subject, comprising administrating to the subject an effective amount of peripheral monocytes induced by granulocyte colony stimulating factor (GCSF) or a combination of GCSF and an interleukin relative to GCSF. Specifically, monocytes can be induced by injecting GCSF into the body of an organism, and peripheral monocytes are collected from the peripheral blood of the organism to obtain the peripheral monocytes in the method of the present invention.

In the present invention, in addition to GCSF, peripheral monocytes can be inducted by a combination of GCSF and an interleukin relative to GCSF, such as interleukin-3 (IL-3) and interleukin-6 (IL-6), etc.

In one embodiment of the present invention, peripheral monocytes are inducted by GCSF or a combination of GCSF and an interleukin relative to GCSF in a living body, and then isolated from the blood. Therefore, the peripheral monocytes in the method of the present invention can be in a form of a living cell extract, comprising components such as blood, body fluids, and other cells.

Preferably, the peripheral monocytes in the method of the present invention are stem cells with surface antigen CD34. CD34 surface antigen is a highly glycosylated trans-membrane glycoprotein, and is selectively expressed on the surface of hematopoietic stem cells (such as peripheral monocytes) of humans or other mammals, and gradually decreases to disappear with the maturation of the cells. The stem cells with surface antigen CD34 in the method of the present invention may be from bone marrow, peripheral blood, or a combination thereof.

The method of the present invention can be used for improving skin appearance, especially for skin aging. In particular, the method of the present invention can be used to promote the production of hyaluronic acid in skin, promote the production of elastic fibers in skin, and/or reduce the loss of collagen in skin. In addition, the method of the present invention also can improve skin firmness, improve skin fullness, promote skin metabolism, and improve skin structure (including thinning the skin epidermis and increasing the elasticity of the dermis). The method of the present invention achieves the following effects via the above mechanisms: reducing the striae (such as forehead wrinkles and nasolabial folds) on the skin, reducing wrinkles, preventing wrinkles, reducing discoloration of skin, improving the color of skin, whitening the skin, and reducing skin pigmentation.

Specifically, it is believed that the method of the present invention can be used to reduce the size of skin pores, improve skin luster, transparency or the degree of tension, improve antioxidant activity, improve skin flexibility or softness, improve the expression level of procollagen or collagen, promote skin reconstruction, improve the repair and function of skin vasospasm, improve skin contour appearance, supply skin essential nutrients or attenuated ingredients due to aging or menopause, improve the communications among skin cells, increase the proliferation or replication of cells, improve the attenuated skin metabolism due to aging or menopause, improve the skin humidity, improve or accelerate cell regeneration, reduce skin sensitivity, and/or improve skin elasticity and resilience, etc.

Because the peripheral monocytes in the method of the present invention can gather in the hair follicles to maintain the activity of hair follicles, promote the activity of hair follicles, and promote hair growth, the method of the present invention has the effects of reducing hair loss, promoting the activation of hair follicle cells, and promoting hair growth.

In the present invention, the peripheral monocytes can be administrated to a subject optimally along with at least one of collagen, hyaluronic acid, a growth factor, and a chemokine of stem cells. Growth factors and chemokine of stem cells can improve or maintain the growth and activity of peripheral monocytes, and the examples of the growth factors and chemokine of stem cells include a platelet factor (PF), GCSF, interleukin relative to GCSF (such as interleukin-3 (IL-3) and interleukin-6 (IL-6)), vascular endothelial growth factor (VEGF), fibroblast growth factors (FGF), and epidermal growth facto (EGF), etc.

In addition, the peripheral monocytes can be administered to a subject by any suitable manner without particular limits. For example, the peripheral monocytes can be administered by application onto the skin surface of the subject or by intravenous injection or subcutaneous injection.

In one embodiment of the present invention, the peripheral monocytes are stem cells with surface antigen CD34, and are administered in a form of a composition. Herein, the concentration of the stem cells with surface antigen CD34 in the composition is about $10^2$ to about $10^9$ cells per micro liter of the composition, and preferably about $10^5$ to about $10^9$ cells per micro liter of the composition.

When the peripheral monocytes in the method of the present invention are in the form of a living cell extract and are administered in the form of a composition, the content of the living cell extract is about 0.001 wt % to about 20 wt %, and preferably about 0.05 wt % to about 10 wt %, more preferably from 0.5 wt % to about 5 wt %, based on the total weight of the composition.

In the method of the present invention, the aforesaid composition has the effects of improving skin appearance and/or reducing hair loss. The composition comprises an effective amount of peripheral monocytes induced by GCSF or a combination of GCSF and an interleukin relative to GCSF, and can be of any suitable form without particular limits. For example, the composition can be in a form of emulsion, cream, or gel for external use, such as a skin care product, cosmetic, etc., and is applied to the skin surface. The composition can also be prepared in the form of infusion for subcutaneous or intravenous injection, such as a suspension, an intravenous injection, a powder injection, a suspension injection, a powder-suspension injection, etc., and is administered by subcutaneous or intravenous injection.

The dosage of the aforesaid composition may be adjusted according to the age of the treated subject and the purpose of the application (such as reducing skin wrinkles or reducing discoloration of skin). The usage frequency may also be optionally adjusted. Other components and content thereof are dependent on the final form of the composition. For instance, when the composition is prepared as a skin care product, any suitable and appropriate amount of emulsion, perfume, and other active components for improving skin quality, such as collagen and hyaluronic acid, may be added therein. In general, any component can be added in the composition, as long as it has no adverse influence on the effects of the peripheral monocytes in the composition.

The present invention also provides use of the peripheral monocytes induced by granulocyte colony stimulating factor or a combination of GCSF and an interleukin relative to GCSF in improving skin aging. In this regard, the content and embodiments of the use of the peripheral monocytes are as described in the above text.

The detailed technology and preferred embodiments implemented for the present invention are described in the following paragraphs; however, the scope of the present invention is not limited thereby.

Experimental Design

The experimental groups were arranged in accordance with the Latin square design experiment method (see Roger E. Kirk, 1995, Latin Square Design, Corsini Encyclopedia of Psychology, which is incorporated herein in its entirety by reference). The experimental sequence was arranged by the counterbalancing principle.

Experiment 1

Captive Breeding of Pigs

One male (5-month old) and three female Lanyu pigs (6, 7, and 9 years old, respectively) were purchased from the Taitung Animal Propagation Station (TAPS) (Taitung, Taiwan). Each pig was accompanied by the descent registration certificate and a production resume. All of the pigs were bred separately and provided with sufficient space to feed, rest, and excrete waste.

The concrete ground floor of the pigsty was equipped with a high-frame strip ground floor, while the wall was equipped with many automatic water supply equipments. The pigs were allowed free access to water and quota diet and were observed daily. The pigsty had no sharp protrusions, and was in a non-sealed breeding space. The pigs were allowed free access to the outside by sight, smell and sound, and were fed via the experimental animal management method of minimal disease (fed twice per day in limited quantity, and provided with rotative medicaments to perform cleaning and disinfection once or twice per month). The pigs were used in the following tests.

Experiment 2

Collection of Peripheral Blood Stem Cells

Peripheral blood stem cells were collected by a blood separator. Five days before the collection, the ear vein of a male pig was injected with a dose of granulocyte colony stimulating factor (300 μl/0.7 ml, Filgrastim M300) as a growth factor to induce the generation of peripheral monocytes (i.e., the stem cells with surface antigen CD34). Until one day before the collection, hematopoietic stem cells in the bone marrow were rapidly released to the peripheral blood and collected. Herein, the blood was drawn from the jugular vein in to a tube (BD Vacutainer® CPT™ Tube), and was gently shaken and mixed with an anticoagulant, and centrifuged at 1800 g for 15 minutes, 700 g for 5 minutes, and 100 g for 10 minutes thrice to separate the buffy coat rich in white blood cells (WBC) comprising stem cells with surface antigen CD34 (i.e., peripheral monocytes).

Experiment 3

Flow Cytometer Analysis

The buffy coat obtained from Experiment 2 was diluted to $1 \times 10^6$ cells by 1×PBS under 4° C. The diluted cell solution (100 μl) was taken and a CD34 antibody (2 μl) was added thereto, and the sample was placed in a refrigerator at 4° C. for 30 minutes. Then, the cell solution was washed with 1×PBS at 4° C. thrice and centrifuged at 400 g for 5 minutes after each wash. A fluorescent-labeled secondary antibody (1 μl, Alexa Fluor® 546 nm donkey anti-rabbit IgG, invitrogen) was added to the sample, and then the sample was dissolved in 3% BSA/PBS (200 μl) and stored in a refrigerator at 4° C. for 30 minutes. Then, the sample was washed with 1×PBS at 4° C. thrice and centrifuged at 400 g for 5 minutes after each wash. The centrifuged cells were stored in a refrigerator at 4° C. in darkness. Finally, a flow cytometer (BD LSR™ II flow cytometer) was used to analyze the expression level of CD 34 in the blood. The analysis results are shown in Table 1 and FIGS. 1A to 2D.

TABLE 1

|  | Control Group | GCSF injection |
| --- | --- | --- |
| Red blood cell | $9.97 \times 10^6$/μl | $8.2 \times 10^6$/μl |
| White blood cell | $1.89 \times 10^4$/μl | $1.05 \times 10^5$/μl |
| Lymphocyte | 72% | 22% |

TABLE 1-continued

|  | Control Group | GCSF injection |
|---|---|---|
| Intermediate cell | 7.8% | 54% |
| Neutrophil cell | 20.2% | 24% |

Figure 2A:
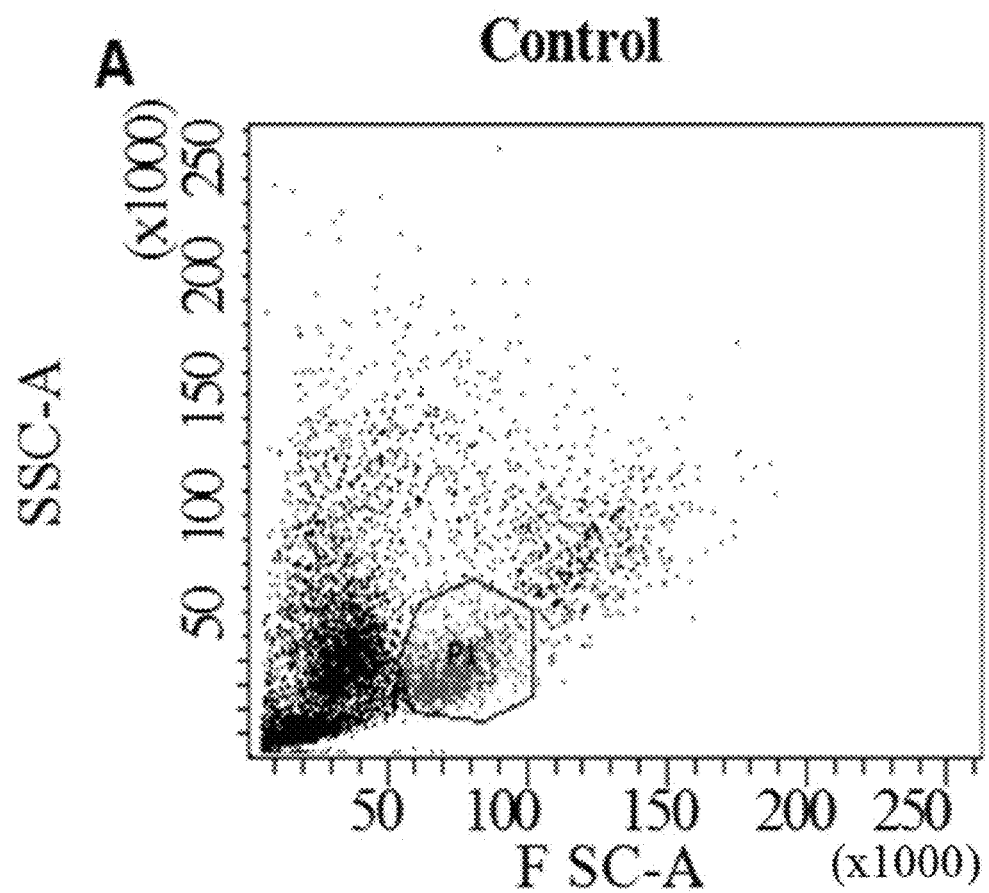
FIG. 2A is a diagram of flow cytometry analysis showing the cell properties (CD34 antigen molecule) of the whole blood cells of a male Lanyu pig, wherein the circled area (P1) shows intermediate cells.
Figure 2B:
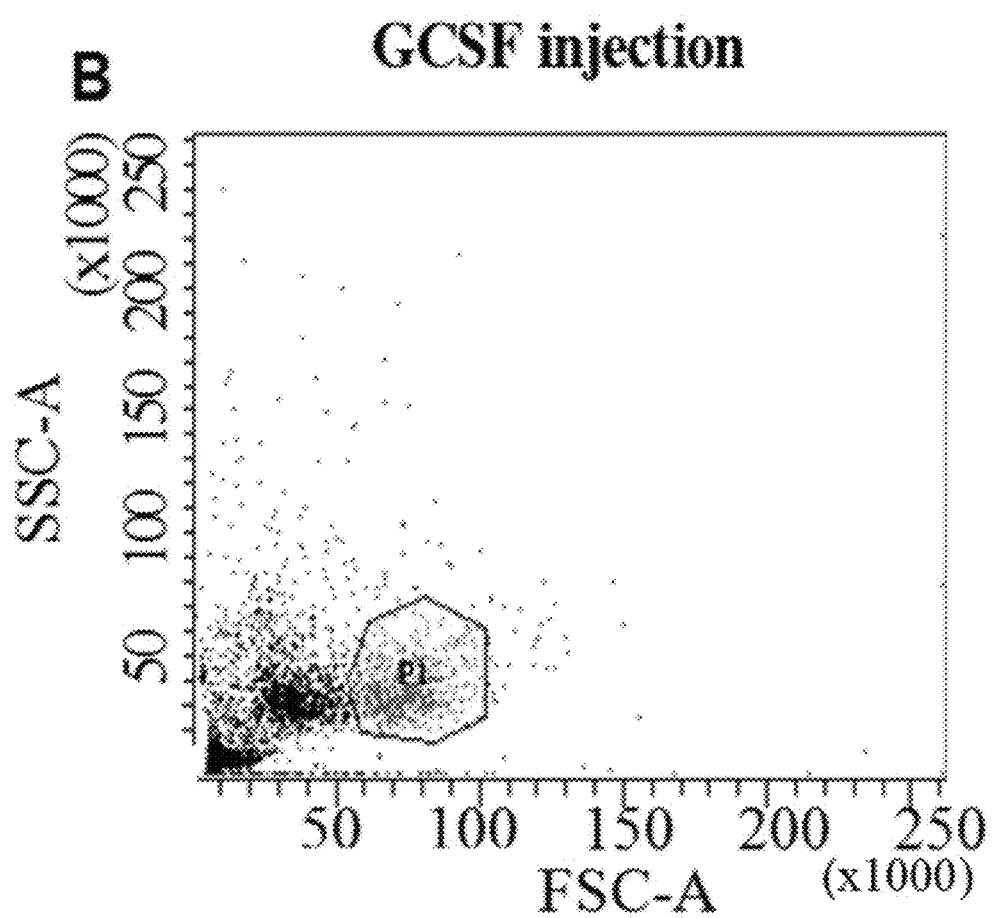
FIG. 2B is a diagram of flow cytometry analysis showing the cell properties (CD34 antigen molecule) of the whole blood cells of a male Lanyu pig injected with GCSF, wherein the circled area (P1) shows intermediate cells.
Figure 2C:
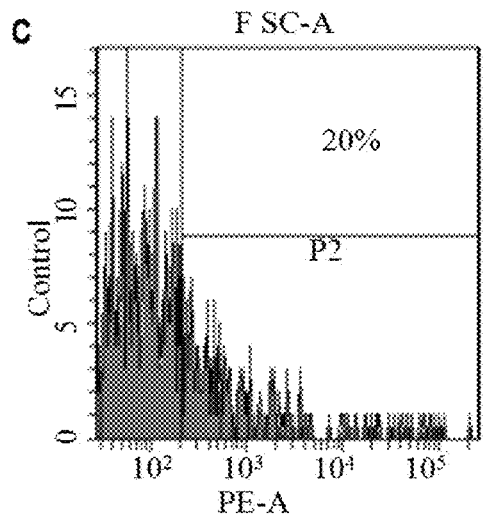
FIG. 2C is a diagram showing the result of the flow cytometry analysis of FIG. 2A.
Figure 2D:
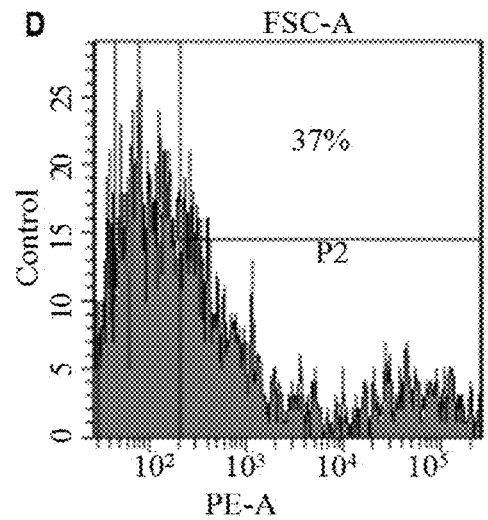
FIG. 2D is a diagram showing the result of the flow cytometry analysis of FIG. 2B.

As shown in Table 1 and FIG. 1D, after being injected with GCSF, the content of white blood cells in the male pigs was increased, and the content of intermediate cells (comprising peripheral monocytes) was increased by 6.9 folds as compared to that before injection. FIG. 2C shows that the stem cells with surface antigen CD34 (i.e., peripheral monocytes) were accounting for 20% of all the intermediate cells. FIG. 2D shows that the stem cells with surface antigen CD34 were accounting for 37% of all the intermediate cells. Therefore, after being injected with GCSF, the content of the stem cells with surface antigen CD34 in the male pigs increased up to 17%. The results of this test show that the generation of stem cells with surface antigen CD34 can be induced by the injection of GCSF. The induced peripheral monocytes were used in the following tests.

Experiment 4

Administration of Peripheral Monocytes

Figure 3:
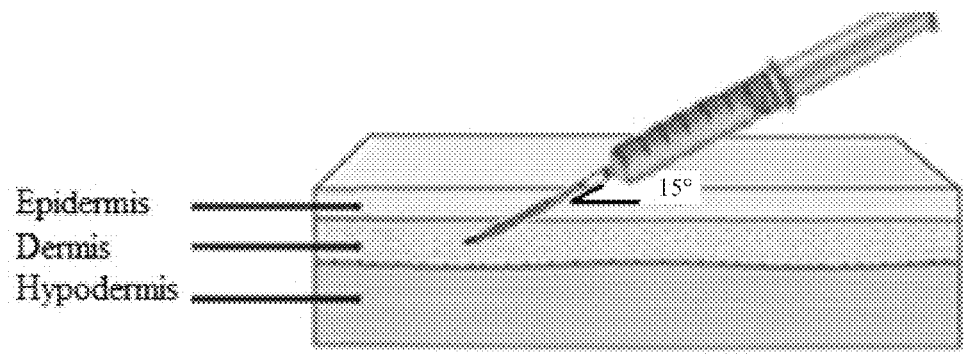
FIG. 3 is a schematic diagram showing the manner for injecting the peripheral monocytes in the present invention.

The buffy coat comprising the stem cells with surface antigen CD34 obtained from Experiment 2 was injected to the dermis of the pigs according to the manner shown in FIG. 3, wherein the needle insertion angle was 15° with respect to the epidermis, and the needle insertion depth was 0.3 cm. After the administration of the stem cells with surface antigen CD34 for one or two weeks, the change in skin of these pigs was observed by the following biochemical analysis methods.

Experiment 5

Preparation and Biopsy of Skin Tissue

First, the hair on the skin area to be biopsied of the pigs was cut by an electric shaver. Then, the surgical site was disinfected by 75% alcohol, and 1 cm square pieces of the skin tissue was biopsied (the depth of biopsy was about 8 mm to see the fat layer). The biopsied sample was fixed in 10% formalin solution (neutral buffered formalin, Surgipath) to keep the initial state of the proteins in the tissue, and was dehydrated by a tissue dehydration machine (Leica TP1020). First, a cassette comprising the skin tissue was put into a tissue dehydration machine, and the tissue was sequentially processed by fixation, dehydration, washing, and rinsing (irrigation of wax). The water in the tissue will be replaced by paraffin after such process. The process was as follows: 10% formalin solution for 1 hour (fixation); double distilled water for 30 minutes (rinsing); 80% alcohol for 1 hour (dehydration); 95% alcohol for 1 hour (dehydration); 95% alcohol for 1 hour (dehydration); 100% alcohol for 1 hour (dehydration); 100% alcohol for 1 hour (dehydration); 100% alcohol for 2 hours (dehydration); xylene for 1 hour (washing); xylene for 2 hours (washing); paraffin wax for 1 hour (rinsing); paraffin wax for 2 hours (rinsing); the dehydrated tissue was embedded with paraffin (tissue block system TBS 88, Medite) into a paraffin block and sectioned by a hand-cranked paraffin section machine (Shandon AS325, Leica, Germany), and the thickness of each section was 3 μm to 5 μm.

Experiment 6

Skin Tissue Stain

Hematoxylin-Eosin Stain

Negatively charged nucleic acid has a stronger affinity to a positively charged alkaline dye (Hematoxylin staining solution). In contrast, cell plasma comprising alkaline substances has a higher affinity to a positively charged acid dye (eosin staining solution). Therefore, after being stained by hematoxylin and eosin, the nucleus will become blue; the cytoplasm, muscle fibers, and collagen fibers will become red with different shades; and the red cells will become orange-red. The staining steps were as follows: the skin tissue was biopsied (5 μm/section); heated at 55° C. for 30 minutes; dewaxed in xylene and rehydrated in alcohol; stained in hematoxylin solution (Sigma, MS-16) for 2 minutes; and washed by running water for 15 minutes. Then, the sample was stained in eosin Y (Sigma, E4382) for 1 minute, and washed by running water for 15 minutes. Finally, the sample was dehydrated in alcohol and mounted by mounting medium. The sample was dried in a hood for 1 day, and observed under a microscope and recorded by using a CCD digital camera system (OLYMPUS, DP70) to take pictures.

Masson's Trichrome Stain/Gelatinous Fiber Stain

Masson's trichrome stain/gelatinous fiber stain is a histochemistry stain, which is used to identify the collagen fiber. In an acidic environment, it can selectively stain collagen fibers and muscle fibers. After the collagen fiber was treated by acid, the biobrich scarlet leaked out from collagen and turned into blue when stained by aniline blue. The staining steps were as follows: the skin tissue was biopsied (5 μm/section); heated at 55° C. for 30 minutes; dewaxed in xylene and rehydrated in alcohol; soaked in Mordant for 30 minutes; stained in Carrazi's hematoxylin solution for 40 minutes; washed by running water for 10 minutes; stained by 0.75% Orange G solution for 1 minute; washed by 1% ice-cold acetic acid twice; stained in Masson B stain solution for 10 minutes; washed by 1% ice-cold acetic acid twice; stained in 2.5% phosphomolybdic-phosphotungstic acid for 10 minutes; washed by 1% ice-cold acetic acid twice; stained in anilin blue for 15 minutes; soaked in 1% ice-cold acetic acid twice; and dehydrated in alcohol and mounted by a mounting medium. Then, the sample was dried in a hood for 1 day, and observed under a microscope and recorded by using a CCD digital camera system (OLYMPUS, DP70) to take pictures.

Elastic Stain (Modified Verhoff's)

Elastic stain is a staining method used to identify elastin, wherein the stained elastin turns into blue-black. The staining steps were as follows: the skin tissue was biopsied (3 μm/section); heated at 55° C. for 30 minutes; dewaxed in xylene and rehydrated in alcohol; stained by a working elastic stain solution for 15 minutes; washed by running water; stained by a 2% Ferric Chloride Differentiating Solution for 20 seconds; washed by running water; stained by a 5% sodium thiosulfate solution for 1 minute; washed by running water; stained in a Van Gieson's solution for 3 minutes; and dehydrated in alcohol and mounted by a mounting medium. Then, the sample was dried in a hood for 1 day, and observed under a microscope and recorded by using a CCD digital camera system (OLYMPUS, DP70) to take pictures.

Mucicarmine Stain (Modified Southgate's)

Mucicarmine stain is a staining method specific to mucine. Mucine is secreted from the epidermis cells and connective tissue. Carmine and aluminium trichloride from Carmine-aluminium can bind with negatively charged sulfate group and carboxyl group and turn red. The staining steps were as follows: the skin tissue was biopsied (5 μm/section); heated at 55° C. for 30 minutes; dewaxed in xylene and rehydrated in alcohol; washed by double distilled water; stained by hematoxylin for 3 minutes; washed by running water for 2 minutes; stained by a Bluing reagent for 30 seconds; soaked in double distilled water; stained in a activated Mucicarmine solution (33% Mucicarmine) for 1 hour; rapidly washed by running water and soaked in double distilled water; stained in a tartrazine solution for 1 minute; rapidly washed by running water and soaked in double distilled water; and dehydrated in alcohol and mounted by a mounting medium. Then, the sample was dried in a hood for 1 day, and observed under a microscope and recorded by using a CCD digital camera system (OLYMPUS, DP70) to take pictures.

Immunhistochemistry (IHC)

Immunofluorescence (IF) stain was used to detect the expression of specific antigens in the tissues. The staining steps were as follows: the skin tissue was biopsied (3 μm/section); heated at 55° C. for 30 minutes; dewaxed in xylene and rehydrated in alcohol; heated in an antigen recovery buffer solution at 121° C. for 10 minutes; the tissue was circled by a DAKO pen; soaked in a 1×PBS solution (containing 3% hydrogen peroxide) at room temperature for 10 minutes to inactivate the intrinsic reductase; washed by a rinse buffer (1×PBS+0.3% TritonX-100) once; treated with a 1×PBS solution (containing 5% FBS) to block non-specific binding; washed with a rinse buffer (1×PBS +0.05% TritonX-100) once; the primary antibodies (hyaluronic acid and CD44, Abcam) diluted in an appropriate fold (1:100 to 1:200) were added to the sample, and the reaction proceeded at room temperature for 2 hours or at 4° C. overnight; washed with a rinse buffer (1×PBS+0.05% TritonX-100) thrice; the secondary antibody diluted in an appropriate fold (1:5000) was added to the sample and the reaction proceeded at room temperature for 1 hour; washed with a rinse buffer (1×PBS+ 0.05% TritonX-100) thrice; a DAB color reagent (3,3'-Diaminobenzidine, LSAB2 Kit, DAKO, Calif., USA) was added to the sample for 10 minutes. The positive result will show a red-brown color while the negative result will show no color. Then, the sample was counter stained in hematoxylin for 1 minute; excessive hematoxylin was washed out; soaked in tap water for 10 minutes; and dehydrated in alcohol and mounted by mounting medium. Then, the sample was dried in a hood, observed under a microscope, and recorded by using a CCD digital camera system (OLYMPUS, DP70) to take pictures.

[Statistical Analysis]

Among the three female Lanyu pigs, the analysis results of each group were represented by "mean±SD." The data of normal distribution was determined by the variation of a Student's t-test distribution experiment, while the data of non-normal distribution was correlated using Mann-Whitney U test. P values of less than 0.05 were considered to be statistically significant.

[Test Result]

Figure 4:
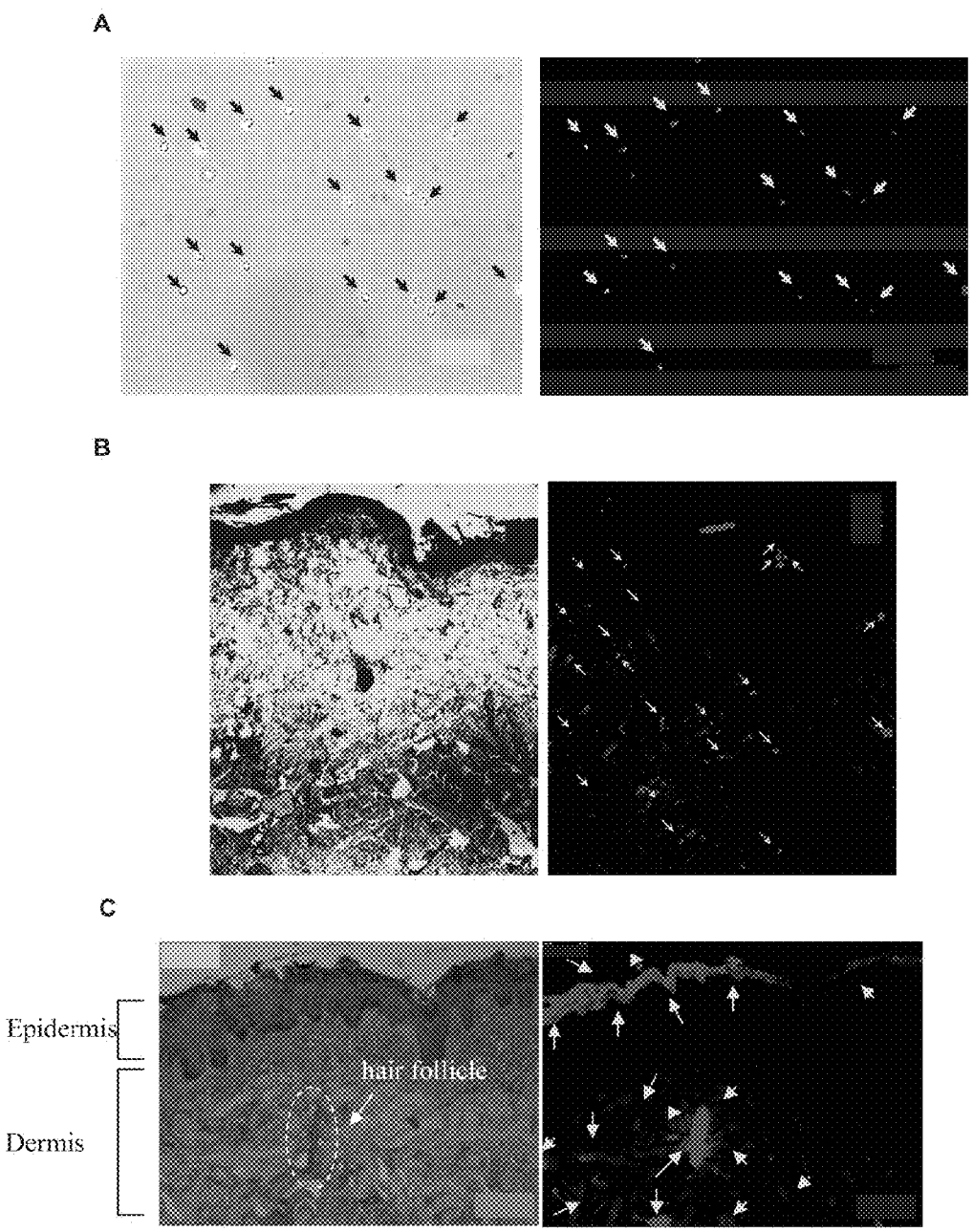
FIG. 4A is a fluorescence microscope picture showing the fluorescent-labeled intermediate cells obtained from a male Lanyu pig injected with GCSF.
FIG. 4B is a fluorescence microscope picture (the right figure) and a picture showing tissue morphology (the left figure) of the biopsied skin tissue obtained one week after the fluorescent-labeled intermediate cells were injected into a 90-month old female Lanyu pig according to the manner shown in FIG. 3.
FIG. 4C is a fluorescence microscope picture (the right figure) and a picture showing the tissue morphology (the left figure) of the biopsied skin tissue obtained two weeks after the fluorescent-labeled intermediate cells were injected into a 90-month old female Lanyu pig according to the manner shown in FIG. 3.
Figure 5:
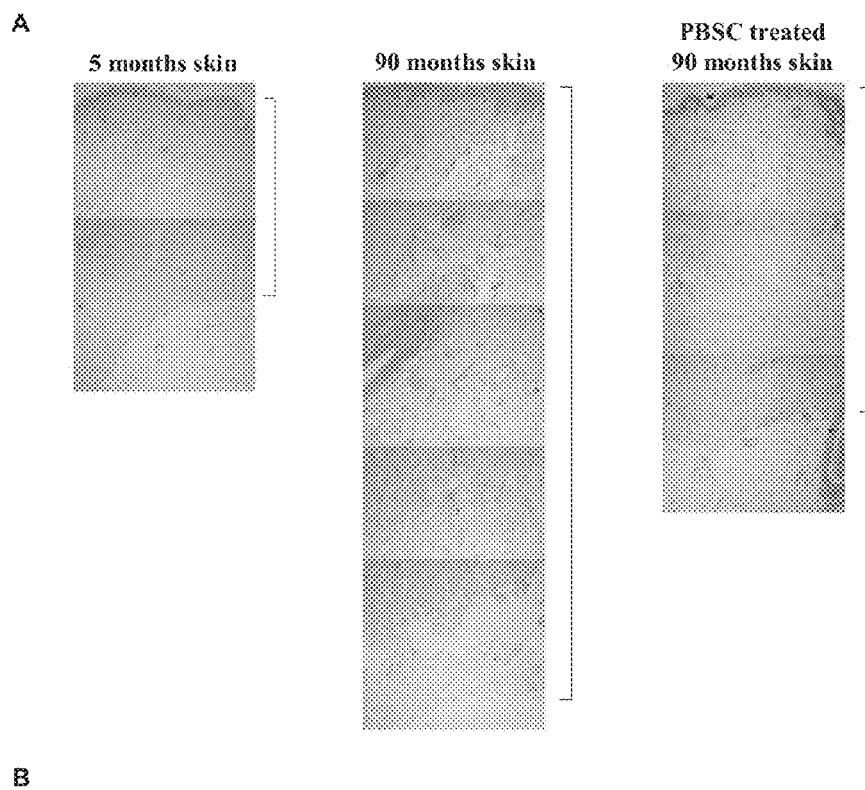
FIG. 5A is a picture showing the skin structure of a 5-month old pig (the left figure, the control group) and a picture showing the change of the skin structure of a 90-month old female Lanyu pig before and after (the middle figure and right figure) injected with peripheral monocytes.
FIG. 5B is a quantitative column diagram showing each skin layer in FIG. 5A.
Figure 5:
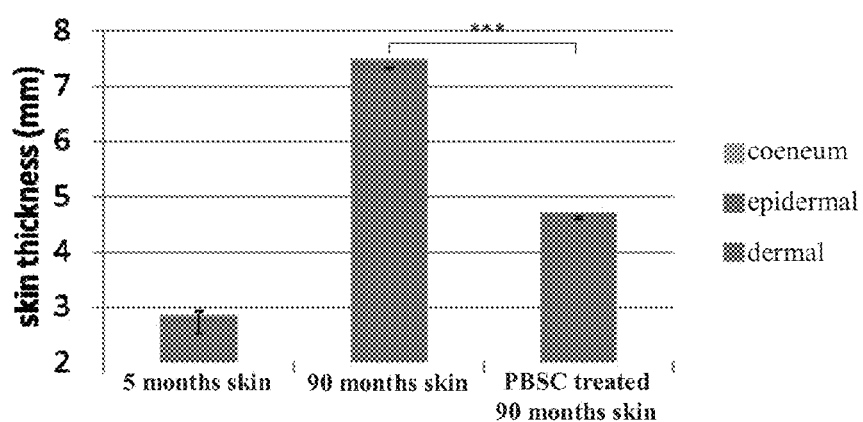

The analytical results of Examples 5 and 6 are shown in FIGS. 4A to 7B. FIG. 4A shows the result of the fluorescent-labeled intermediate cells (comprising peripheral monocytes) obtained from a male Lanyu pig injected with GCSF. The left figure of FIG. 4A shows the cell morphology under visible light, and the right figure shows the cell morphology under a microscope.

FIG. 4B shows the results of the biopsied skin tissue observed by a fluorescence microscope (the right figure) and the tissue morphology (the left figure) obtained one week after the fluorescent-labeled intermediate cells (comprising the peripheral monocytes) were injected into a 90-month old female Lanyu pig. The results show that after one week of the injection, the intermediate cells gathered in the hair follicles and distributed in the dermis.

FIG. 4C shows the results of the biopsied skin tissue observed by a fluorescence microscope (the right figure) and the tissue morphology (the left figure) obtained two weeks after the fluorescent-labeled intermediate cells (comprising the peripheral monocytes) were injected into a 90-month old female Lanyu pig. The results show that after two weeks of the injection, the intermediate cells gathered in the hair follicles and epidermis, and distributed in the dermis. Because a hair follicle is the niche of hair follicle stem cells, hair follicle stem cells are closely related to the activity of hair follicles and the growth of hairs. FIGS. 4B and 4C show that the intermediate cells (comprising the peripheral monocytes) gathered in the hair follicles, indicating that the hair follicle released a homing factor due to a lack of growth factor to attract the stem cells to maintain the activity of hair follicles and the growth of hair. The intermediate cells have various growth factors and can enter into a hair follicle through the induction of homing factors. Therefore, the peripheral monocytes in the method of the present invention can help maintain the health of hair follicles, reduce hair loss, and promote new hair growth.

FIG. 5A shows the comparison of the change of the skin structure of a 90-month old female Lanyu pig before and after being injected with the peripheral monocytes. FIG. 5A shows that the epidermis of the skin before injection (the middle figure) had significant wrinkles, and the skin structure was loose and arranged unevenly. The epidermis of the skin after injection (the right figure) was delicate, while the skin firmness and skin fullness were improved. The skin of a 5-month old pig with young skin quality was used as the control group.

FIG. 5B shows the thickness of each skin layer of a female pig, indicating that the injection of the peripheral monocytes can significantly reduce the thickness of dermis and improve the skin structure.

Figure 6:
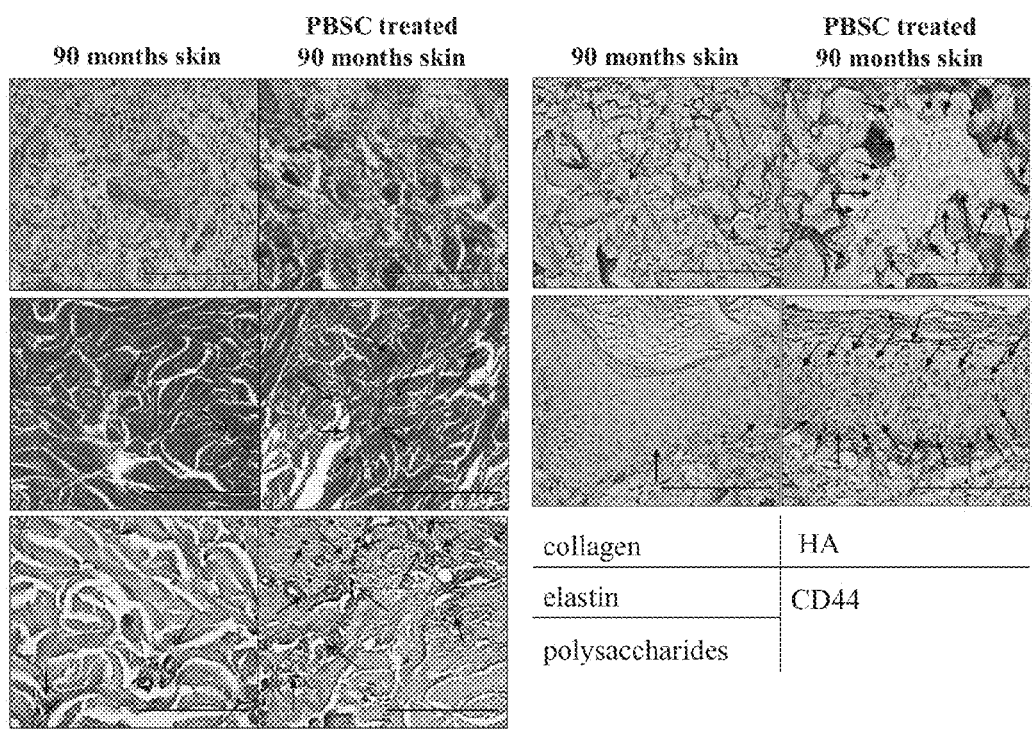
FIG. 6 is a immunhistochemistry staining picture showing the collagen, elastin, polysaccharide, hyaluronic acid, and CD44 in the skin of a 90-month old female Lanyu pig before and after injected with peripheral monocytes.
Figure 7:
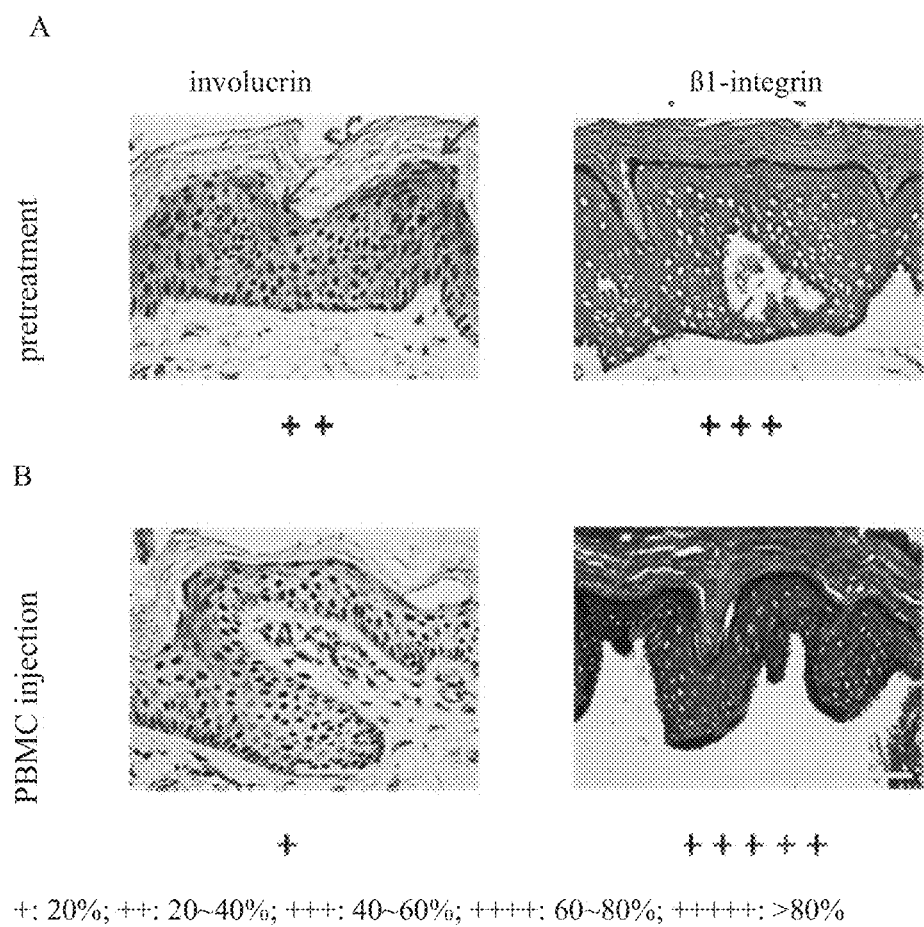
FIGS. 7A and 7B are immunhistochemistry staining pictures showing the involucrin and the β1 integrin of keratinocytes in the skin of a 90-month old female Lanyu pig before and after injected with peripheral monocytes.

FIG. 6 shows the analytical result of the immunhistochemistry staining of the skin of a 90-month old female Lanyu pig before and after being injected with the peripheral monocytes and analyzed by using specific antigens of collagen, elastin (an indicator of skin elasticity), polysaccharide (an indicator of skin water retention), and hyaluronic acid and CD44 (indicators of scar eliminating capacity). Table 2 shows the quantitative results of FIG. 6.

TABLE 2

|  | The skin of a 90-month old female pig | The skin of a 90-month old female pig injected with peripheral monocytes |
|---|---|---|
| collagen | + | +++++ |
| elastin | + | ++ |
| polysaccharide | + | +++ |
| hyaluronic acid | + | ++++ |
| CD44 | + | +++++ |

+: <20%;
++: 20 to 40%;
+++: 40 to 60%;
++++: 60 to 80%;
+++++: >80%

Table 2 and FIG. 6 indicate that the skin of 90-month old female Lanyu pigs injected with peripheral monocytes shows the following effects: (1) reducing the loss of collagen; (2) improving skin firmness and improving skin fullness; (3) improving the skin water retention ability; and (4) reducing the striae and wrinkles.

FIGS. 7A and 7B show the analytical result of the immunhistochemistry staining of the skin of a 90-month old female Lanyu pig before and after being injected with the peripheral monocytes and analyzed by using specific antigens of involucrin (an indicator of keratinization level) and the β1 integrin of keratinocytes. FIGS. 7A and 7B show that the skin of the female Lanyu pig had a higher keratinization level and a higher keratinocyte ratio before being injected with the peripheral monocytes, while the proliferation level of the keratinocyte was significantly higher than the keratinization level to increase the skin metabolic rate. Thus, peripheral monocytes can promote skin renewal and metabolism.

The above examples show that in respect to the biochemical function, the peripheral monocytes in the method of the present invention can promote the production of hyaluronic acid in skin, promote the production of elastin (elastic fiber) in skin, and reduce the loss of collagen in skin; and in respect to the physiological effect, it can improve skin firmness, improve skin fullness, promote skin metabolism, and improve skin structure (including thinning the skin epidermis and increasing the elasticity of the dermis). Therefore, the method of the present invention can achieve the effects of reducing the striae on skin, reducing wrinkles, preventing wrinkles, reducing the discoloration of skin, thereby, improving the appearance of skin.

The above disclosure is related to the detailed technical contents and inventive features thereof. People skilled in this field may proceed with a variety of modifications and replacements based on the disclosures and suggestions of the invention as described without departing from the characteristics thereof Nevertheless, although such modifications and replacements are not fully disclosed in the above descriptions, they have substantially been covered in the following claims as appended.

What is claimed is:

1. A method for improving skin appearance of a subject, comprising administering to the subject an effective amount of a buffy coat comprising peripheral monocytes in a form of a composition, wherein the peripheral monocytes are stem cells with surface antigen CD34 induced by granulocyte colony stimulating factor (GCSF) or a combination of GCSF and at least one of interleukin-3 (IL-3) and interleukin-6 (IL-6), and wherein the concentration of the stem cells with surface antigen CD34 in the composition is about $10^2$ to about $10^9$ cells per micro liter of the composition, such that the subject's skin exhibits a biochemical or physiological response evidenced by an increased level of at least one characteristic selected from the group consisting of collagen, elastin, polysaccharides, hyaluronic acid and CD44.

2. The method as claimed in claim 1, wherein the peripheral monocytes are induced by a combination of GCSF and at least one of interleukin-3 (IL-3) and interleukin-6 (IL-6).

3. The method as claimed in claim 1, wherein the composition is a living cell extract.

4. The method as claimed in claim 1, wherein the buffy coat is administered to the subject along with at least one of collagen, hyaluronic acid, a growth factor, and a chemokine of stem cells.

5. The method as claimed in claim 1, wherein the stem cells with surface antigen CD34 are from bone marrow, peripheral blood, or a combination thereof.

6. The method as claimed in claim 1, wherein the concentration of the stem cells with surface antigen CD34 is about $10^5$ to about $10^9$ cells per micro liter of the composition.

7. The method as claimed in claim 1, wherein the buffy coat is administered by application onto the skin surface of the subject or by intravenous injection or subcutaneous injection.

8. The method as claimed in claim 1, which is effective for at least one of promoting the production of hyaluronic acid in skin, promoting the production of elastic fibers in skin, and reducing the loss of collagen in skin.

9. The method as claimed in claim 1, which is effective for at least one of improving skin firmness, improving skin fullness, promoting skin metabolism, and improving skin structure.

10. The method as claimed in claim 1, which is effective for at least one of reducing the striae on skin, reducing wrinkles, and preventing wrinkles.

11. The method as claimed in claim 1, which is effective for at least one of reducing discoloration of skin, improving the color of skin, whitening the skin, and reducing skin pigmentation.

* * * * *